United States Patent [19]

Wu et al.

[11] Patent Number: 5,866,741

[45] Date of Patent: Feb. 2, 1999

[54] TRANSALKYLATION/ HYDRODEALKYLATION OF A $C_9+$ AROMATIC COMPOUNDS WITH A ZEOLITE

[75] Inventors: An-hsiang Wu, Bartlesville; Charles A. Drake, Nowata, both of Okla.

[73] Assignee: Phillips Petroleum Company, Bartlesville, Okla.

[21] Appl. No.: 899,109

[22] Filed: Jul. 23, 1997

[51] Int. Cl.[6] .................................. C07C 5/22; C07C 4/12
[52] U.S. Cl. ..................... 585/475; 585/485; 585/489; 585/488; 585/486
[58] Field of Search .................... 585/475, 485, 585/484, 488, 486

[56] References Cited

U.S. PATENT DOCUMENTS

| | | | |
|---|---|---|---|
| 3,948,758 | 4/1976 | Bonacci et al. | 208/92 |
| 4,891,458 | 1/1990 | Innes et al. | 585/323 |
| 4,911,823 | 3/1990 | Chen et al. | 208/67 |
| 5,030,787 | 7/1991 | Absil et al. | 585/475 |
| 5,387,723 | 2/1995 | Knifton et al. | 568/698 |
| 5,406,016 | 4/1995 | Cook et al. | 585/475 |
| 5,453,553 | 9/1995 | Sivasanker et al. | 585/467 |

FOREIGN PATENT DOCUMENTS 1343172  1/1974  United Kingdom .

*Primary Examiner*—Glenn Caldarola
*Assistant Examiner*—Thuan D. Dang
*Attorney, Agent, or Firm*—Lucas K. Shay

[57] ABSTRACT

A catalyst composition, a process for producing the composition and a hydrocarbon conversion process for converting a $C_9+$ aromatic compound to a $C_6$ to $C_8$ aromatic hydrocarbon such as a xylene are disclosed. The composition comprises a zeolite having impregnated thereon an activity promoter selected from the group consisting of molybdenum, molybdenum oxides, lanthanum, lanthanum oxides, and combinations of two or more thereof. The composition can be produced by incorporating the activity promoter into the zeolite. The hydrocarbon conversion process comprises contacting a fluid which comprises a $C_9+$ aromatic compound with the catalyst composition under a condition sufficient to effect the conversion of a $C_9+$ aromatic compound to a $C_6$ to $C_8$ aromatic hydrocarbon.

28 Claims, No Drawings

TRANSALKYLATION/ HYDRODEALKYLATION OF A C$_9$+ AROMATIC COMPOUNDS WITH A ZEOLITE

FIELD OF THE INVENTION

This invention relates to a catalyst composition useful for converting a C$_9$+ aromatic compound to a C$_6$ to C$_8$ aromatic hydrocarbon, to a process for producing the composition and to a process for using the composition in a hydrodealkylation process.

BACKGROUND OF THE INVENTION

It is well known to those skilled in the art that aromatic hydrocarbons are a class of very important industrial chemicals which find a variety of uses in petrochemical industry. Recent efforts to convert gasoline to more valuable petrochemical products have therefore focused on the aromatization of gasoline to aromatic hydrocarbons by catalytic cracking in the presence of a catalyst. The aromatic hydrocarbons produced by the aromatization process include C$_6$ to C$_8$ hydrocarbons such as benzene, toluene and xylenes (hereinafter collectively referred to as BTX) which can be useful feedstocks for producing various organic compounds and polymers. However, heavier, less useful aromatic compounds are also produced during the aromatization process. It is, therefore, highly desirable to convert these compounds to the more useful BTX.

Though a number of catalysts have been used in a hydrodealkylation or transalkylation process, the conversion of a C$_9$+ aromatic compound and the selectivity to BTX are generally not as high as one skilled in the art would desire. Furthermore, a catalyst used in the hydrodealkylation or transalkylation of these heavier aromatic compounds is generally deactivated in a rather short period because of depositions of carbonaceous material such as, for example, coke on the surface of the catalyst.

Accordingly, there is an ever-increasing need to develop a catalyst and a process for converting these heavier and less useful aromatic compounds (mainly trimethyl- and tetramethylbenzenes) to the more valuable BTX hydrocarbons while simultaneously suppressing the coke formation. Such development would also be a significant contribution to the art and to the economy.

SUMMARY OF THE INVENTION

An object of this invention is to provide a catalyst composition which can be used to convert a C$_9$+ aromatic compound to a C$_6$ to C$_8$ aromatic hydrocarbon. Also an object of this invention is to provide a process for producing the catalyst composition. Another object of this invention is to provide a process which can employ the catalyst composition to convert C$_9$+ aromatic compounds to C$_6$ to C$_8$ aromatic compounds. An advantage of the catalyst composition is that it decreases coke deposits thereon and exhibits high transalkylation activity, satisfactory yield of xylenes and BTX, and good stability. Other objects and advantages will become more apparent as this invention is more fully disclosed hereinbelow.

According to a first embodiment of the present invention, a composition which can be used as a catalyst for converting a C$_9$+ aromatic compound to a C$_6$ to C$_8$ aromatic hydrocarbon is provided. The composition can comprise a zeolite having incorporated therein an activity promoter.

According to a second embodiment of the invention, a process for producing a composition which can be used as catalyst in a hydrocarbon conversion is provided. The process can comprise (1) optionally calcining a zeolite to produce a calcined zeolite; (2) contacting a zeolite or a calcined zeolite with an activity promoter precursor selected from the group consisting of silicon-containing compounds, phosphorus-containing compounds, boron-containing compounds, magnesium-containing compounds, tin-containing compounds, titanium-containing compounds, zirconium-containing compounds, molybdenum-containing compounds, germanium-containing compounds, indium-containing compounds, lanthanum-containing compounds, cesium-containing compounds, and combinations of any two or more thereof under a condition sufficient to incorporate the activity promoter into the zeolite to form a modified zeolite; and (3) calcining the modified zeolite.

According to a third embodiment of the present invention, a process which can be used for converting a C$_9$+ aromatic compound to a C$_6$ to C$_8$ aromatics compound is provided which comprises, consists essentially of, or consists of, contacting a fluid which comprises a C$_9$+ aromatic compound, optionally in the presence of an inert fluid such as a hydrogen-containing fluid, with a catalyst composition, which is the same as disclosed above in the first embodiment of the invention, under a condition effective to convert a C$_9$+ aromatic compound to an aromatic hydrocarbon containing 6 to 8 carbon atoms per molecule.

DETAILED DESCRIPTION OF THE INVENTION

According to the first embodiment of the invention, a composition which can be used as catalyst in a transalkylation or hydrodealkylation process for converting a C$_9$+ aromatic compound to a C$_6$ to C$_8$ aromatic hydrocarbon is provided. The composition comprises, consists essentially of, or consists of, a zeolite having incorporated therein, preferably impregnated thereon, an activity promoter selected from the group consisting of silicon, phosphorus, boron, magnesium, tin, titanium, zirconium, molybdenum, germanium, indium, lanthanum, cesium, any oxide thereof, and combinations of two or more thereof wherein the activity promoter is present in the composition in a coke-suppressing amount, or an activity-enhancing amount to improve the conversion of a C$_9$+ aromatic compound, when the composition is used in a transalkylation process.

According to the first embodiment of the invention, the weight ratio of the activity promoter to the zeolite can be any ratio so long as the ratio can enhance or improve the conversion of a C$_9$+ aromatic compound or suppress or reduce the formation or deposition of coke on a zeolite catalyst during the transalkylation process for converting a C$_9$+ aromatic compound to a C$_6$ to C$_8$ aromatic hydrocarbon. Generally, the ratio can be in the range of from about 0.0001:1 to about 1:1, preferably about 0.0005:1 to about 1:1, more preferably about 0.001:1 to about 0.8:1 and most preferably from 0.005:1 to 0.5:1 for an effective hydrocarbon conversion and coke reduction or suppression. Alternatively, the activity promoter can be present in the catalyst composition in the range of from about 0.01 to about 50, preferably about 0.05 to about 50, more preferably about 0.1 to about 45, and most preferably 0.5 to 33 grams per 100 grams of the catalyst composition.

If a combination of lanthanum and one or more activity promoters is employed, the atomic ratio of lanthanum to other promoter(s) can be in the range of about 0.01:1 to about 10:1, preferably about 0.1:1 to about 8:1, more preferably about 0.5:1 to about 5:1, and most preferably 1:1 to 3:1. The presently preferred composition is a beta zeolite having impregnated thereon a combination of lanthanum and molybdenum or a combination of their oxides in which the atomic ratio of La to Mo is 0.5 to 3.

According to the present invention, any activity promoter that, as compared to use of a zeolite only, can effect the increase in the conversion of a $C_9+$ aromatic compound to a $C_6$–$C_8$ aromatic hydrocarbon or reduction of coke deposition on the zeolite during the conversion of a $C_9+$ aromatic compound to a $C_6$ to $C_8$ aromatic hydrocarbon can be employed. Presently it is preferred that the activity promoter is selected from the group consisting of silicon, phosphorus, boron, magnesium, tin, titanium, zirconium, molybdenum, germanium, indium, lanthanum, cesium, any oxides thereof and combinations of two or more thereof. The presently most preferred activity promoter is a combination of lanthanum and molybdenum or a combination of their oxides.

The composition can also be characterized by having the following physical characteristics: a micropore surface area, as determined by the BET method using nitrogen, in the range of from about 50 to about 1,000, preferably 50 to 500 $m^2/g$; a micropore pore volume in the range of from about 0.1 to about 2.0, preferably about 0.1 to about 1.0 ml/g; an average micropore pore diameter in the range of from about 0.1 to about 500, preferably about 1 to about 200 Å; and a porosity of more than about 20%.

Any commercially available zeolites can be employed as a starting material of the process of the second embodiment of the invention. Examples of suitable zeolites include, but are not limited to, those disclosed in Kirk-Othmer Encyclopedia of Chemical Technology, third edition, volume 15 (John Wiley & Sons, New York, 1991). The presently preferred zeolite is a beta zeolite.

Any methods known to one skilled in the art for incorporating a compound or a portion thereof into a zeolite such as, for example, impregnation or extrusion can be employed for producing the composition of the present invention. However, it is presently preferred the composition be produced by the process disclosed in the second embodiment of the invention.

According to the second embodiment of the invention, a zeolite, preferably a beta zeolite, can be optionally contacted with one or more suitable binders in a liquid, preferably aqueous medium, to form a zeolite-binder mixture. Any binders known to one skilled in the art for use with a zeolite are suitable for use herein. Examples of suitable binder include, but are not limited to, clays such as for example, kaolinite, halloysite, vermiculite, chlorite, attapulgite, smectite, montmorillonite, illite, saconite, sepiolite, palygorskite, and combinations of two or more thereof; diatomaceous earth; aluminas such as for example α-alumina and γ-alumina; silicas; alumina-silica; aluminum phosphate; aluminum chlorohydrate; and combinations of two or more thereof. Because these binders are well known to one skilled in the art, description of which is omitted herein. The weight ratio of a zeolite to a binder can be in a wide range and generally in the range of from about 200:1 to about 0.1:1, preferably 100:1 to 0.01:1.

The zeolite and the binder can be well mixed by any means known to one skilled in the art such as stirring, blending, kneading, or extrusion, following which the zeolite-binder mixture can be dried in air at a temperature in the range of from about 20° to about 200° C., preferably about 25° to about 175° C., and most preferably 25° to 150° C. for about 0.5 to about 50 hours, preferably about 1 to about 30 hours, and most preferably 1 to 20 hours, preferably under atmospheric pressure. Thereafter, the dried, zeolite-binder mixture can be further calcined, if desired, in air at a temperature in the range of from about 300° to 1000° C., preferably about 350° to about 750° C., and most preferably 450° to 650° C. for about 1 to about 30 hours to prepare a calcined zeolite-binder. If a binder is not desired, a zeolite can also be calcined under similar conditions to remove any contaminants, if present.

A zeolite, a calcined zeolite, or a calcined zeolite-binder can be treated with a compound containing an exchangeable ammonium ion to prepare an ammonium-exchanged zeolite. Whether a zeolite is calcined or contains a binder, the process or treatment in the second embodiment is the same for each. For the interest of brevity, only a zeolite is described hereinbelow. Examples of suitable ammonium-containing compounds include, but are not limited to, ammonium sulfate, ammonium chloride, ammonium nitrate, ammonium bromide, ammonium fluoride, and combinations of any two or more thereof. Treatment of the zeolite replaces the original ions such as, for example, alkali or alkaline earth metal ions of the zeolite with predominantly ammonium ions. Techniques for such treatment are well known to one skilled in the art such as, for example, ion exchange with the original ions. For example, a zeolite can be contacted with a solution containing a salt of the desired replacing ion or ions.

Generally, a zeolite can be suspended in an aqueous solution of an ammonium-containing compound. The concentration of the zeolite in the aqueous solution can be in the range of from about 0.01 to about 200, preferably about 0.1 to about 150, more preferably about 1 to about 100, and most preferably 5 to 75 grams per liter. The amount of the ammonium-containing compound required depends on the amount of the original ion(s) to be exchanged. Upon the preparation of the solution, the solution can be subject to a temperature in the range of from about 30° C. to about 200° C., preferably about 40° C. to about 150° C., and most preferably 50° C. to 125° C. for about 1 to about 100 hours, preferably about 1 to about 50 hours, and most preferably 2 to 25 hours depending on desired degrees of ion exchange. The treatment can be carried out under a pressure in the range of from about 1 to about 10 atmospheres (atm), preferably about 1 atm or any pressure that can maintain the required temperature. Thereafter, the treated zeolite can be washed with running water for 1 to about 60 minutes followed by drying and calcining to produce calcined zeolite. The drying and calcining processes can be carried out substantially the same as those disclosed above for the preparation of a calcined zeolite or zeolite-binder.

Generally, the ammonium-exchanged zeolite becomes hydrogen exchanged upon calcination or high temperature treatment such that a predominant proportion of its exchangeable cations are hydrogen ions. The above-described ion exchanges of exchangeable ions in a zeolite is well known to one skilled in the art. See, for example, U.S. Pat. No. 5,516,956, disclosure of which is incorporated herein by reference. Because the ion exchange procedure is well known, the description of which is omitted herein for the interest of brevity.

A zeolite is generally first treated with an activity promoter precursor. According to the second embodiment of the present invention, any activity promoter precursor which can be converted to an activity promoter, as disclosed in the first embodiment of the invention, that, as compared to use of a zeolite only, can effect the improvement of conversion of a $C_9+$ aromatic compound to BTX or xylene or the reduction of coke in a transalkylation process can be employed. Presently it is preferred that an activity promoter precursor be selected from the group consisting of molybdenum-containing compounds, lanthanum-containing compounds, phosphorus-containing compounds, boron-containing compounds, magnesium-containing compounds, tin-containing compounds, titanium-containing compounds, zirconium-containing compounds, germanium-containing compounds, indium-containing compounds, cesium-containing compounds, and combinations of two or more thereof.

Generally any lanthanum-containing compounds which, when incorporated or impregnated into a zeolite are effective to enhance the conversion of a $C_9+$ aromatic compound, can be used in the present invention. Examples of suitable lanthanum-containing compounds include, but are not limited to, lanthanum acetate, lanthanum carbonate, lanthanum octanoate, lanthanum fluoride, lanthanum chloride, lanthanum bromide, lanthanum iodide, lanthanum nitrate, lanthanum perchlorate, lanthanum sulfate, lanthanum titanate, and combinations of two or more thereof.

Similarly, any molybdenum containing compounds which, when incorporated or impregnated into a zeolite are effective to enhance the conversion of a $C_9+$ aromatic compound can be used in the present invention. Suitable molybdenum-containing compounds include, but are not limited to, molybdenum(II) chloride, molybdenum(III) chloride, molybdenum(II) acetate, molybdenum(IV) chloride, molybdenum(V) chloride, molybdenum(VI) fluoride, molybdenum hexacarbonyl, molybdenum sulfide, sodium molybdates, potassium molybdates, molybdenum (VI) oxychloride, molybdenum(IV) sulfide, ammonium tetrathiomolybdate, ammonium molybdate, ammonium dimolybdate, ammonium heptamolybdate(VI) and combinations of two or more thereof.

Examples of the other activity promoters can be found in applicants' copending application Ser. No. 08/705,926 in which the term "acid site modifier" instead of activity promoter is used therein, the disclosure of which is herein incorporated by reference.

Generally, a zeolite, calcined zeolite, zeolite-binder, calcined zeolite-binder, can be combined with such activity promoter precursor in any suitable weight ratios which would result in the weight ratios of an activity promoter to a zeolite disclosed in the first embodiment of the invention. Presently it is preferred that such combination be carried out in a suitable liquid, preferably an aqueous medium, to form an incipient wetness zeolite-precursor mixture or a modified zeolite.

The zeolite and the precursor are well mixed. In the next step of the process, the modified zeolite is subjected to calcination under a condition that can include a temperature in the range of from about 300° C. to about 1000° C., preferably about 350° C. to about 750° C., and most preferably 400° C. to 650° C. under a pressure that can accommodate the temperatures and is generally in the range of from about 1 to about 10, preferably about 1, atmospheres for a period in the range of from about 1 to about 30, preferably about 1 to about 20, and most preferably 1 to 15 hours. Upon completion of incorporating or impregnating the activity promoter into the zeolite by calcination, a promoted zeolite is formed.

The composition of the invention then can be, if desired, pretreated with a reducing agent before being used in a hydrodealkylation or a transalkylation process. The presently preferred reducing agent is a hydrogen-containing fluid which comprises molecular hydrogen ($H_2$) in the range of from 1 to about 100, preferably about 5 to about 100, and most preferably 10 to 100 volume %. The reduction can be carried out at a temperature, in the range of from about 250° C. to about 800° C. for about 0.1 to about 10 hours preferably about 300° C. to about 700° C. for about 0.5 to about 7 hours, and most preferably 350° C. to 650° C. for 1 to 5 hours.

According to the third embodiment of the present invention, a process comprises, consists essentially of, or consists of contacting a fluid stream with a catalyst composition, optionally in the presence of an inert gas, preferably a hydrogen-containing fluid, under a condition sufficient to enhance or effect the conversion of a hydrocarbon to a mixture rich in $C_6$ to $C_8$ aromatic hydrocarbons wherein said fluid stream comprises a hydrocarbon or hydrocarbon mixture which can comprise $C_9+$ aromatic compounds, paraffins, olefins, naphthenes. The catalyst composition is the same as that disclosed in the first embodiment of the invention which can be prepared by the second embodiment of the invention.

The term "fluid" is used herein to denote gas, liquid, vapor, or combinations thereof. The term "increase, improve, or enhance" refers to increased BTX in the product employing the catalyst composition as compared to employing an untreated zeolite. Examples of a hydrocarbon include, but are not limited to, butane, isobutanes, pentane, isopentanes, hexane, isohexanes, cyclohexane, methylcyclohexane, heptane, isoheptanes, octane, isooctanes, nonanes, decanes, undecanes, dodecanes, tridecanes, tetradecanes, pentadecanes, hexadecanes, butenes, isobutene, pentenes, hexenes, 1,2,3-trimethylbenzene, 1,2,4-trimethylbenzene, 1,3,5-trimethylbenzene, 1,2,3,4-tetramethylbenzene, 1,2,3,5-tetramethylbenzene, 1,2,4,5-tetramethylbenzene, n-propylbenzene, 3-ethyltoluene, 4-ethyltoluene, 3-n-propyltoluene, 4-n-propyltoluene, 1,3-diethylbenzene, naphthalenes, and combinations of any two or more thereof. In some feed fluids, such as, for example, gasoline can comprise some benzene, toluene, ethylbenzene, and xylenes.

Any fluid which contains a $C_9+$ aromatic compound can be used as the feed for the process of this invention. Generally, the fluid feed stream can also contain olefins, naphthenes (cycloalkanes), or some aromatic compounds. Examples of suitable, available fluid feeds include, but are not limited to, gasolines from catalytic oil cracking processes, pyrolysis gasolines from thermal cracking of saturated hydrocarbons, naphthas, gas oils, reformates, and combinations of any two or more thereof. The origin of this fluid feed is not critical. Though particular composition of a feed is not critical, a preferred fluid feed is derived from gasolines which generally contain more paraffins (alkanes) than combined content of olefins, cycloalkanes, and aromatic compounds.

Any fluid which contains a $C_9+$ aromatic compound as disclosed above can also be used as the feed for the process of this invention. A $C_9+$ aromatic compound can have the formula of $R'_qAr$ wherein each R' is a hydrocarbyl radical having 1 to about 15 carbon atoms and is independently selected from the group consisting of alkyl radicals, aryl radicals, alkaryl radicals, aralkyl radicals, alkenyl radicals, and combinations of any two or more thereof, q is a whole number from 1 to 5, and Ar is an aryl or arylene group. The origin of the $C_9+$ aromatic compounds feed is not critical. However, a preferred fluid feed is a $C_9+$ aromatic compound derived from the heavies fraction of a product from a paraffin, in particular gasoline, aromatization reaction. Generally, this heavies fraction contains primarily trimethylbenzenes such as 1,2,3-trimethylbenzene, 1,2,4-trimethylbenzene, and 1,3,5-trimethylbenzene; tetramethylbenzenes such as 1,2,3,4-tetramethylbenzene, 1,2,3,5-tetramethylbenzene and 1,2,4,5-tetramethylbenzene; and naphthalenes. Additionally, n-propylbenzene, 3-ethyltoluene, 4-ethyltoluene, 3-n-propyltoluene, 4-n-propyltoluene, and 1,3-diethylbenzene can also be present in the fluid.

In a hydrodealkylation process benzene, toluene, ethylbenzene and xylenes are generally substantially absent from the fluid, i.e., the amount of each of these aromatic hydrocarbons is less than about 0.1 weight % in the fluid. However, in a transalkylation process, one or more of benzene, toluene, ethylbenzene and xylenes can be present in the feed to effect a significant alkylation of the lower aromatic hydrocarbons by the $C_9+$ aromatic compounds, i.e., significant transalkylation occurs. The condition for carrying out hydrodealkylation and transalkylation can be substantially the same as disclosed hereinbelow.

Any hydrogen-containing fluid which comprises, consists essentially of, or consists of, molecular hydrogen ($H_2$) can be used in the process of this invention. This hydrogen-containing fluid can contain $H_2$ in the range of from about 1 to about 100, preferably about 5 to about 100, and most preferably 10 to 100 volume %. If the $H_2$ content in the fluid is less than 100%, the remainder of the fluid may be any inert gas such as, for example, $N_2$, He, Ne, Ar, steam, or combinations of any two or more thereof, or any other fluid which does not significantly affect the process or the catalyst composition used therein.

The contacting of a fluid feed stream containing a hydrocarbon with a hydrogen-containing fluid in the presence of the catalyst composition can be carried out in any technically suitable manner, in a batch or semicontinuous or continuous process, under a condition effective to convert a hydrocarbon to a $C_6$ to $C_8$ aromatic hydrocarbon. Generally, a fluid stream as disclosed above, preferably being in the vaporized state, is introduced into a suitable hydroprocessing reactor having a fixed catalyst bed, or a moving catalyst bed, or a fluidized catalyst bed, or combinations of any two or more thereof by any means known to one skilled in the art such as, for example, pressure, meter pump, and other similar means. Because a hydroprocessing reactor and process therewith are well known to one skilled in the art, the description of which is omitted herein for the interest of brevity. The condition of the process of the invention can include a weight hourly space velocity of the fluid feed stream in the range of about 0.01 to about 100, preferably about 0.05 to about 50, and most preferably 0.1 to 30 g feeding catalyst/hour. The hydrogen-containing fluid (gas) hourly space velocity generally is in the range of about 1 to about 10,000, preferably about 5 to about 7,000, and most preferably 10 to 10,000 $ft^3$ $H_2/ft^3$ catalyst/hour. Generally, the pressure can be in the range of from about 10 to about 2000 psig, preferably about 100 to about 1000 psig, and most preferably 200 to 750 psig, and the temperature is about 250° to about 1000° C., preferably about 300° to about 750° C., and most preferably 400° to 650° C.

The process effluent generally contains a light gas fraction comprising hydrogen and methane; a $C_2$–$C_3$ fraction containing ethylene, propylene, ethane, and propane; an intermediate fraction including non-aromatic compounds having greater than 3 carbon atoms; a BTX aromatic hydrocarbons fraction (benzene, toluene, ortho-xylene, meta-xylene and para-xylene); and a $C_9+$ fraction which contains aromatic compounds having 9 or more carbon atoms per molecule. Generally, the effluent can be separated into these principal fractions by any known methods such as, for example, fractionation distillation. Because the separation methods are well known to one skilled in the art, the description of which is omitted herein. The intermediate fraction can be fed to an aromatization reactor to be converted to aromatic hydrocarbons; methane, ethane, and propane can be used as fuel gas or as a feed for other reactions such as, for example, in a thermal cracking process to produce ethylene and propylene. The olefins can be recovered and further separated into individual olefins by any method known to one skilled in the art. The individual olefins can then be recovered and marketed. The BTX fraction can be further separated into individual $C_6$ to $C_8$ aromatic hydrocarbon fractions. Alternatively, the BTX fraction can further undergo one or more reactions either before or after separation to individual $C_6$ to $C_8$ hydrocarbons so as to increase the content of the most desired BTX aromatic hydrocarbon. Suitable examples of such subsequent $C_6$ to $C_8$ aromatic hydrocarbon conversions are disproportionation of toluene (to form benzene and xylenes), transalkylation of benzene and xylenes (to form toluene), and isomerization of meta-xylene and/or ortho-xylene to para-xylene.

After the catalyst composition has been deactivated by, for example, coke deposition or feed poisons, to an extent that the feed conversion and/or the selectivity to the desired ratios of olefins to BTX have become unsatisfactory, the catalyst composition can be reactivated by any means known to one skilled in the art such as, for example, calcining in air to burn off deposited coke and other carbonaceous materials, such as oligomers or polymers, preferably at a temperature of about 400° to about 1000° C. The optimal time periods of the calcining depend generally on the types and amounts of deactivating deposits on the catalyst composition and on the calcination temperatures. These optimal time periods can easily be determined by those possessing ordinary skills in the art and are omitted herein for the interest of brevity.

The following examples are presented to further illustrate this invention and are not to be construed as unduly limiting the scope of the present invention.

EXAMPLE I

This example illustrates the preparation of beta zeolite-containing compositions essentially according to the second embodiment of the invention.

Catalyst A was produced from a commercial beta zeolite BEA, which contained 30 weight % alumina as binder and was obtained from UOP, Inc. (Des Plaines, Ill.). The BEA zeolite was calcined at 538° C. for 6 hours to produce catalyst A. This was used as control.

This zeolite BEA (10 g) was impregnated with a solution containing 0.375 g of ammonium molybdate (($NH_4$)$_6MO_7O_{24}·4H_2O$) and 4.50 g of $H_2O$ by incipient wetness method at about 25° C. The ammonium molybdate-impregnated zeolite BEA was then calcined in air (muffle furnace) for 6 hours at 538° C. to produce 10.1 g of catalyst B containing 2.036 weight % molybdenum by calculation.

Catalyst C was prepared by impregnating 10.0 g of the commercial zeolite BEA with 8 g of 15 weight % lanthanum nitrate ($La(NO_3)_3·6H_2O$) solution, following the procedure of catalyst B, to produce 10.02 g of a La-promoted zeolite (catalyst C) containing 3.789 weight % lanthanum by calculation.

The procedure for producing catalyst C was repeated. In this run, the calcined La-promoted zeolite (10.16 g) was further impregnated with a solution containing 7.33 g of 6 weight % ammonium heptamolybdate (($NH_4$)$_6MO_7O_{24}·4H_2O$) solution by the incipient wetness method described above. The lanthanum- and molybdate-impregnated zeolite BEA was calcined in air for 6 hours at about 538° C. to produce 10.48 g La/Mo promoted zeolite (catalyst D) containing 3.789 weight % La and 2.280 weight % Mo by calculation (atomic ratio of La/Mo=1.148).

Catalyst E was obtained by first soaking 25 g of the calcined zeolite BEA (catalyst A) with 20.52 g of a 30 weight % La(NO$_3$)$_3$·6H$_2$O solution in water followed by calcination at 538° C. for 6 hours to produce 27.07 g of calcined La-promoted zeolite. Of this 27.07 g, 6.21 g was impregnated with 3.74 g of 6 weight % ammonium heptamolybdate solution. The final product weighted 6.34 g and contained 7.295 weight % molybdenum by calculation (atomic ratio of La/Mo=2.60).

EXAMPLE II

This example illustrates the use of the zeolite materials (catalysts A, B, C, D, and E) described in Example I in a transalklylation of a feed comprising C$_9$+ aromatic compounds and toluene to produce a product containing a higher concentration of BTX than the feed. The composition of aromatic compounds, up to 12 carbons per molecule, of the feed used for the transalkylation is shown in Table I. There were some paraffins, isoparaffins, and naphthenes as well as numerous unidentified components in the feed that are not shown in Table I.

TABLE I

| Aromatics (weight %) | C$_6$ | 0.000 |
|---|---|---|
| | C$_7$ (toluene) | 50.248 |
| | C$_8$ | 0.411 |
| | C$_9$ | 11.315 |
| | C$_{10}$ | 12.664 |
| | C$_{11}$ | 9.457 |
| | C$_{12}$ | 3.001 |
| | Total | 87.096 |
| Sulfur (ppmw) | | 658 |

A stainless-steel reactor tube (inner diameter: 2.5 cm; length: 50 cm) was filled with a 20 cm bottom layer of Alundum® alumina (inert, low surface area alumina, provided by Norton Company, Worcester, Mass.), 5 ml of one of the zeolite materials described in Example I, and a 20 cm top layer of Alundum®. The reactor and its content were pre-heated from room temperature to the desired reaction temperature of about 575° C. The zeolite-containing catalysts were pretreated with flowing hydrogen gas at a rate of 260 ml per minute at 500° C. starting at 25° C. and ramping at 10° C./min. The reaction pressure was set at 500 psig. A liquid feed as shown in Table I was introduced into the heated reactor at a rate of 20 ml/hour. The product, which exited the reactor, was cooled, analyzed by means of an online gas chromatograph at intervals of about 1 hour. The results are also summarized in Table II.

TABLE II

| Catal[a] | Time[b] (hr) | Temp (°C.) | % Conv C$_9$+ | % Conv[c] Naph | wt % Xyln's | Avg wt % Coke/hr[d] |
|---|---|---|---|---|---|---|
| A | 6.93 | 500 | 35.9 | 48.0 | 6.34 | 4.522 |
| B | 7.00 | 503 | 45.5 | 33.0 | 7.06 | 2.555 |
| C | 6.83 | 499 | 35.5 | 47.1 | 2.90 | ND |
| D | 6.86 | 499 | 69.7 | 84.3 | 25.41 | 2.652 |
| E | 6.98 | 496 | 63.5 | 64.1 | 18.15 | 2.038 |

[a]See catalyst designations in Example I.
[b]Time of transalkylation or hydrodealkylation reaction.
[c]Conversion of naphthalenes.
[d]Coke was determined at the end of the reaction by removing the catalysts from the reactor and determined with a thermal gravimetric analyzer (TGA), manufactured by TA Instruments, New Castle, Delaware; ND, not determined.

The results shown in Table II demonstrate that use of a beta zeolite as catalyst (catalyst A) in transalkylation reaction had a low conversion of C$_9$+ aromatic compound as well as naphthalenes. Impregnation of the zeolite with molybdenum (catalyst B) improved the conversion of C$_9$+ aromatic compounds to xylenes and significantly reduced the coke rate in a transalkylation process as compared to the control (catalyst A), but did not enhance the conversion of naphthalenes. Table II also shows that impregnation of zeolite beta with lanthanum (catalyst C) did not improve the conversion of C$_9$+ aromatic compound and naphthalene. Table II further shows that in a transalkylation process, impregnation of beta zeolite with both lanthanum and molybdenum (catalysts D and E) had considerably higher conversion of C$_9$+aromatic compounds (including naphthalenes), higher xylenes yield, and (catalyst E) lower coke than catalyst A, B, and C.

The results shown in the above examples clearly demonstrate that the present invention is well adapted to carry out the objects and attain the ends and advantages mentioned as well as those inherent therein. While modifications may be made by those skilled in the art, such modifications are encompassed within the spirit of the present invention as defined by the disclosure and the claims.

That which is claimed is:

1. A process comprising contacting a fluid, which comprises a C$_9$+ aromatic compound, with a catalyst composition under a condition sufficient to effect the conversion of said C$_9$+ aromatic compound to a C$_6$ to C$_8$ aromatic hydrocarbon wherein said catalyst composition comprises a beta zeolite having incorporated therein an activity promoter comprising (1) lanthanum or lanthanum oxide and (2) molybdenum or molybdenum oxide.

2. A process according to claim 1 wherein said C$_9$+ aromatic compound has the formula of R'$_q$Ar wherein each R' is a hydrocarbyl radical having 1 to about 15 carbon atoms and is independently selected from the group consisting of alkyl radicals, aryl radicals, alkaryl radicals, aralkyl radicals, alkenyl radicals, and combinations of any two or more thereof, q is a whole number from 1 to 5, and Ar is an aryl group.

3. A process according to claim 1 wherein the weight ratio of said activity promoter to said zeolite is in the range of from about 0.0001:1 to about 1:1.

4. A process according to claim 1 wherein the weight ratio of said activity promoter to said zeolite is in the range of from 0.005:1 to 0.5:1.

5. A process according to claim 1 wherein said atomic ratio of lanthanum to molybdenum is in the range of from about 0.01:1 to about 10:1.

6. A process according to claim 1 wherein the weight ratio of said activity promoter to said zeolite is in the range of from about 0.005:1 to about 0.5:1 and the atomic ratio of lanthanum to molybdenum is in the range of from about 0.1:1 to about 8:1.

7. A process according to claim 1 wherein the weight ratio of said activity promoter to said zeolite is in the range of from 0.005:1 to 0.5:1 and the atomic ratio of lanthanum to molybdenum is in the range of from 1:1 to 3:1.

8. A process according to claim 1 wherein said contacting is carried out in the presence of a hydrogen-containing fluid.

9. A process according to claim 8 wherein said condition comprises a liquid hourly space velocity of said fluid in the range of about 0.1 to about 30 g feed/g catalyst/hour, a gas hourly space velocity of said hydrogen-containing fluid in the range of about 10 ft$^3$ gas/ft$^3$ catalyst/hour to about 5,000 ft$^3$/ft$^3$ catalyst/hour, a molar ratio of hydrogen to said C$_9$+ aromatic compound in the range of about 0.5:1 to about 5:1, a pressure in the range of about 50 psig to about 750 psig, and a temperature in the range of about 250° C. to about 1000° C.

10. A process comprising contacting a fluid, which comprises a C$_9$+ aromatic compound, with a catalyst composition under a condition sufficient to effect the conversion of said C$_9$+ aromatic compound to a C$_6$ to C$_8$ aromatic hydrocarbon wherein said catalyst composition consists essentially of a beta zeolite having impregnated thereon a binder and an activity promoter comprising (1) lanthanum or lanthanum oxide and (2) molybdenum oxide wherein the weight ratio of said activity promoter to said zeolite is in the range of from about 0.0001:1 to about 1:1 and the atomic ratio of lanthanum to molybdenum is in the range of from about 0.01:1 to about 10:1.

11. A process according to claim 10 wherein the weight ratio of said activity promoter to said zeolite is in the range of from 0.005:1 to 0.5:1 and the atomic ratio of lanthanum to molybdenum is in the range of from 1:1 to 3:1.

12. A process according to claim 11 wherein said contacting is carried out in the presence of a hydrogen-containing fluid.

13. A process according to claim 12 wherein said hydrogen-containing fluid is hydrogen.

14. A process according to claim 13 wherein said condition comprises a liquid hourly space velocity of said fluid in the range of about 0.1 to about 30 g feed/g catalyst/hour, a gas hourly space velocity of said hydrogen-containing fluid in the range of about 10 ft$^3$ gas/ft$^3$ catalyst/hour to about 5,000 ft$^3$/ft$^3$ catalyst/hour, a molar ratio of hydrogen to said C$_9$+ aromatic compound in the range of about 0.5:1 to about 5:1, a pressure in the range of about 50 psig to about 750 psig, and a temperature in the range of about 250° C. to about 1000° C.

15. A transalkylation process comprising contacting, in the presence of a hydrogen-containing fluid, a fluid comprising a C$_9$+ aromatic compound and a C$_6$–C$_8$ aromatic hydrocarbon with a catalyst composition under a condition sufficient to effect the conversion of said C$_9$+ aromatic compound to a C$_6$ to C$_8$ aromatic hydrocarbon wherein said catalyst composition is prepared by the steps comprising: (1) contacting a beta zeolite with a molybdenum-containing compound and a lanthanum-containing compound under a condition sufficient to impregnate said activity promoter onto said beta zeolite to form a modified zeolite; and (2) calcining said modified beta zeolite.

16. A process according to claim 15 wherein said lanthanum-containing compound is selected from the group consisting of lanthanum acetate, lanthanum carbonate, lanthanum octanoate, lanthanum fluoride, lanthanum chloride, lanthanum bromide, lanthanum iodide, lanthanum nitrate, lanthanum perchlorate, lanthanum sulfate, lanthanum titanate and combinations of two or more thereof.

17. A process according to claim 15 wherein said molybdenum-containing compound is selected from the group consisting of molybdenum chlorides, molybdenum acetates, molybdenum fluorides, molybdenum hexacarbonyl, molybdenum sulfides, sodium molybdates, potassium molybdates, molybdenum oxychlorides, ammonium tetrathiomolybdate, ammonium molybdate, ammonium dimolybdate, ammonium heptamolybdate, and combinations of two or more thereof.

18. A process according to claim 15 wherein said activity promoter precursor is selected from the group consisting of lanthanum acetate, lanthanum carbonate, lanthanum octanoate, lanthanum fluoride, lanthanum chloride, lanthanum bromide, lanthanum iodide, lanthanum nitrate, lanthanum perchlorate, lanthanum sulfate, lanthanum titanate, molybdenum chlorides, molybdenum acetates, molybdenum fluorides, molybdenum hexacarbonyl, molybdenum sulfides, sodium molybdates, potassium molybdates, molybdenum oxychlorides, ammonium tetrathiomolybdate, ammonium molybdate, ammonium dimolybdate, ammonium heptamolybdate, and combinations of two or more thereof.

19. A process according to claim 18 wherein said lanthanum-containing compound is lanthanum nitrate and said molybdenum-containing compound is ammonium heptamolybdate.

20. A process according to claim 19 wherein said hydrogen-containing fluid is hydrogen.

21. A process according to claim 19 wherein said C$_6$–C$_8$ aromatic hydrocarbon is toluene.

22. A process according to claim 15 wherein said hydrogen-containing fluid is hydrogen.

23. A process according to claim 15 wherein said C$_6$–C$_8$ aromatic hydrocarbon is toluene.

24. A process comprising contacting a fluid which comprises a C$_9$+ aromatic compound and at least one C$_6$–C$_8$ aromatic hydrocarbon, in the presence of hydrogen, with a catalyst composition under a condition sufficient to effect the conversion of a C$_9$+ aromatic compound to a C$_6$ to C$_8$ aromatic hydrocarbon wherein said catalyst composition comprises a beta zeolite having impregnated thereon lanthanum and molybdenum wherein the atomic ratio of lanthanum to molybdenum is in the range of from 1:1 to 3:1 and the weight % of the sum of lanthanum and molybdenum in said catalyst composition is in the range of from 0.5 to 33%.

25. A process according to claim 24 wherein said catalyst composition comprises an alumina-bound beta zeolite.

26. A process according to claim 25 wherein said C$_6$–C$_8$ aromatic hydrocarbon is toluene.

27. A process according to claim 24 wherein said C$_6$–C$_8$ aromatic hydrocarbon is toluene.

28. A transalkylation process comprising contacting, in the presence of a hydrogen, a fluid comprising a C$_9$+ aromatic compound and toluene with a catalyst composition under a condition sufficient to effect the conversion of said C$_9$+ aromatic compound to a C$_6$ to C$_8$ aromatic hydrocarbon wherein said catalyst composition is produced by the process comprising: (1) contacting a beta zeolite with ammonium heptamolybdate and lanthanum nitrate under a condition sufficient to impregnate said ammonium heptamolybdate and lanthanum nitrate onto said zeolite to form a modified zeolite; and (2) calcining said modified zeolite.

* * * * *